United States Patent
Morita et al.

(10) Patent No.: US 7,501,995 B2
(45) Date of Patent: *Mar. 10, 2009

(54) SYSTEM AND METHOD FOR PRESENTATION OF ENTERPRISE, CLINICAL, AND DECISION SUPPORT INFORMATION UTILIZING EYE TRACKING NAVIGATION

(75) Inventors: Mark M. Morita, Arlington Heights, IL (US); Prakash Mahesh, Schaumburg, IL (US); Thomas A. Gentles, Algonquin, IL (US)

(73) Assignee: General Electric Company, Schenectady, NY (US)

( * ) Notice: Subject to any disclaimer, the term of this patent is extended or adjusted under 35 U.S.C. 154(b) by 576 days.

This patent is subject to a terminal disclaimer.

(21) Appl. No.: 11/039,152

(22) Filed: Jan. 19, 2005

(65) Prior Publication Data
US 2006/0109237 A1 May 25, 2006

Related U.S. Application Data (60) Provisional application No. 60/631,045, filed on Nov. 24, 2004.

(51) Int. Cl.
*G09G 5/00* (2006.01)
*A61B 5/00* (2006.01)
(52) U.S. Cl. .......................... 345/7; 600/300
(58) Field of Classification Search ................. 345/156, 345/7–9; 705/1, 2, 3, 7; 600/300
See application file for complete search history.

(56) References Cited

U.S. PATENT DOCUMENTS

| | | | | |
|---|---|---|---|---|
| 5,886,683 A | * | 3/1999 | Tognazzini et al. | 345/156 |
| 6,152,563 A | | 11/2000 | Hutchinson et al. | |
| 6,847,336 B1 | * | 1/2005 | Lemelson et al. | 345/8 |
| 6,941,313 B2 | * | 9/2005 | Seliger et al. | 705/3 |
| 2004/0061831 A1 | | 4/2004 | Aughey et al. | |
| 2006/0074633 A1 | * | 4/2006 | Mahesh et al. | 704/9 |
| 2006/0074711 A1 | * | 4/2006 | Mahesh et al. | 705/2 |

OTHER PUBLICATIONS

Web page for SensoMotoric Instruments, http://www.smi.de/iv/index.html.
Web page for MicroOptical, http://www.microoptical.net/Products/HomePage.html.

* cited by examiner

*Primary Examiner*—Kevin M Nguyen
(74) *Attorney, Agent, or Firm*—McAndrews, Held & Malloy, Ltd.; Peter J. Vogel; Michael A. Dellapenna (57) ABSTRACT

Certain embodiments of the present invention provide a method and system for using gaze detection to improve information display in a healthcare environment. Certain embodiments of a gaze detection and control system include an information system including information related to at least one image, a display device capable of displaying images and data, and a gaze tracking system for detection a location of a user's gaze with respect to the display device. The gaze tracking system triggers a retrieval of information from the information system based at least in part on the location of the user's gaze, and the retrieved information is displayed at the display device. In an embodiment, the retrieved information is overlaid over an image at the display device. In an embodiment, the gaze tracking system includes at least one camera and/or eyewear, for example.

13 Claims, 4 Drawing Sheets

SYSTEM AND METHOD FOR PRESENTATION OF ENTERPRISE, CLINICAL, AND DECISION SUPPORT INFORMATION UTILIZING EYE TRACKING NAVIGATION

RELATED APPLICATIONS

The present application relates to, and claims priority from, U.S. Provisional Application No. 60/631,045 filed on Nov. 24, 2004, and entitled "System and Method for Presentation of Enterprise, Clinical, and Decision Support Information Utilizing Eye Tracking Navigation".

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to display of information in a healthcare environment. In particular, the present invention relates to use of gaze detection technology to improve selection and display of relevant information in a healthcare environment.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, HIS, RIS, CIS, CVIS, LIS, and/or EMR, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitate operation of an imaging system and related services by an individual operator would be highly desirable.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Hospitals and other healthcare environments currently have many disparate enterprise information systems that are not integrated, networked or in communication with each other. Currently, a practitioner must log on to different systems and search for a patient to retrieve information from the systems on that patient. During a diagnostic interpretation process, when practitioners use a variety of clinical information to make a diagnosis, for example, practitioners must physically locate workstations containing specific information that they are seeking. Practitioners must log-in, navigate to a particular patient, and then "drill down" or locate a specific kernel of information. Practitioners must currently undertake this manual process for each bit of information they are seeking.

For example, a radiologist identifies a mass in a patient's kidney. Before diagnosing, the radiologist is interested in particular lab results, such as PT (blood clotting), Creatinine, Gleason Score, etc. Currently, a radiologist must access different systems to obtain all of the lab results. Thus, the radiologist may be presented with a large amount of information to review. The radiologist then uses a workstation to parse the lab results and identify the specific desired information. The radiologist must then remember the values and interpretation of the values and enter the values and interpretation into his or report. Such a process may be time consuming. Thus, a system and method providing increased integration between systems and information would be highly desirable.

Depending upon vendors and systems used by a practitioner, practitioners, such as radiologists or cardiologists, have only a few options to reference the tools available. First, a request for information from the available tools may be made in paper form. Second, a practitioner may use different applications, such as a RIS, PACS, EMR, HIS, CIS, CVIS, and LIS, to search for patients and examine the information electronically.

In the first case, the practitioner shifts his or her focus away from a reading workstation to search and browse through the paper, which in most cases includes many pieces of paper per patient. This slows down the practitioner and introduces a potential for errors due to the sheer volume of paper. Thus, a system and method that reduce the amount of paper being viewed and arranged by a practitioner would be highly desirable.

In the second case, electronic information systems often do not communicate well across different systems. Therefore, the practitioner must log on to each system separately and search for the patients and exams on each system. Such a tedious task results in significant delays and potential errors. Thus, a system and method that improve communication and interaction between multiple electronic information systems would be highly desirable.

Additionally, even if systems are integrated using mechanisms such as Clinical Context Object Workgroup (CCOW) to provide a practitioner with a uniform patient context in several systems, the practitioner is still provided with too much information to browse through. Too much information from different applications is provided at the same time and slows down the reading and analysis process. There is a need to filter out application components that a user will not need in a routine workflow. Thus, a system and method which manage information provided by multiple systems would be highly desirable.

Currently, a healthcare environment such as an operating room (OR) includes multiple displays (CRT, LCD, etc.) connected to multiple, disparate information and/or imaging systems. The displays may be hanging on boom mounted arms from walls, ceilings, tables, and/or floors, for example. In some healthcare settings, such as an OR, ten or more displays may clutter the room and cause great difficulty for practitioners trying to locate key information without scanning each display.

When practitioners wish to access information from the disparate systems, the practitioners must currently turn their heads to look up at the multiple displays and determine which display holds the desired information. Head movement, particularly during a medical procedure, is neither ergonomically correct nor comfortable for the practitioner. Additionally, such head movement may be very repetitive throughout an examination or procedure. Thus, a system and method that reduce head movement and improves ergonomics in a healthcare environment would be highly desirable.

In addition, multiple displays results in an overabundance of information presented simultaneously to a healthcare practitioner. Thus, too much information on too many displays creates difficulty for a practitioner attempting to locate relevant information. Therefore, there is a need for a system and method to improve identification of key information and reduce display clutter in a healthcare environment.

Further difficulties may arise from having too many displays in a healthcare environment, such as an OR. For example, multiple displays are not cost effective from an information technology perspective. Purchasing multiple displays for one or more rooms represents a significant expense for a healthcare provider. Additionally, for example, multiple displays and/or multiple systems generate additional heat in a healthcare environment. Excess heat contributes to higher electric bills and may pose a health hazard to patients, practitioners, and equipment in a healthcare environment. Therefore, a system that reduces multiple displays in a healthcare environment would be highly desirable.

Thus, there is a need for a system and method to improve retrieval and display of relevant information in a healthcare environment.

BRIEF SUMMARY OF THE INVENTION

Certain embodiments of the present invention provide a method and system for using gaze detection to improve information display in a healthcare environment. Certain embodiments of a gaze detection and control system include an information system including information related to at least one image, a display device capable of displaying images and data, and a gaze tracking system for detection a location of a user's gaze with respect to the display device. The gaze tracking system triggers a retrieval of information from the information system based at least in part on the location of the user's gaze, and the retrieved information is displayed at the display device.

In an embodiment, the retrieved information is overlaid over an image at the display device. In an embodiment, the gaze tracking system includes at least one camera and/or eyewear, for example. The system may also include a conflict resolution module for determining priority and control of the display device among a plurality of users. In an embodiment, a function at the display device may be triggered using a voice command, a gesture, and/or a gaze, for example.

In an embodiment, the system also includes a plurality of perspectives that each save a relation with at least one of a plurality of information sources. The system may also include a medical perspectives manager for associating at least one information source with a perspective. The medical perspectives manager allows a user to access the associated information source(s) using the perspective.

In an embodiment, the system also includes a rules engine that has at least one rule governing availability and/or presentation of information. The system may also include a context manager for obtaining information from the plurality of information sources based on a query and filtering the information based on the rule(s) from the rules engine.

Certain embodiments of a method for displaying medical information based on gaze detection include determining a location of a user's gaze in relation to a reference position, and updating information on a display device based on the user's gaze. In an embodiment, information is updated on the display device based on preferences and/or input from the user, for example.

The method may also include arbitrating between a plurality of users to determine who has control of the display device. In an embodiment, multiple users may be allowed control of information on all or part of the display device. A function may be triggered at the display device using a voice command, a gesture, and/or a gaze, for example Additionally, the method may include overlaying information on top of information previously displayed at the display device. The method may further include defining at least one perspective that personalizes information relevant to the user. In an embodiment, information available on the display is filtered based on one or more rules.

In an embodiment, a computer-readable storage medium includes a set of instructions for a computer directed to displaying information. The set of instructions includes a gaze detection routine for determining a location at which a user is looking at a display, and a display routine for displaying, on the display, information associated with the location. The set of instructions may also include a rules-based context manager for selecting filtering the information for display. In an embodiment, the information includes data and/or image(s), for example. Additionally, the set of instructions may include a perspectives management routine for customizing layout of the information for display. Furthermore, the gaze detection routine may map the location at the display to a location in content displayed by the display routine.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
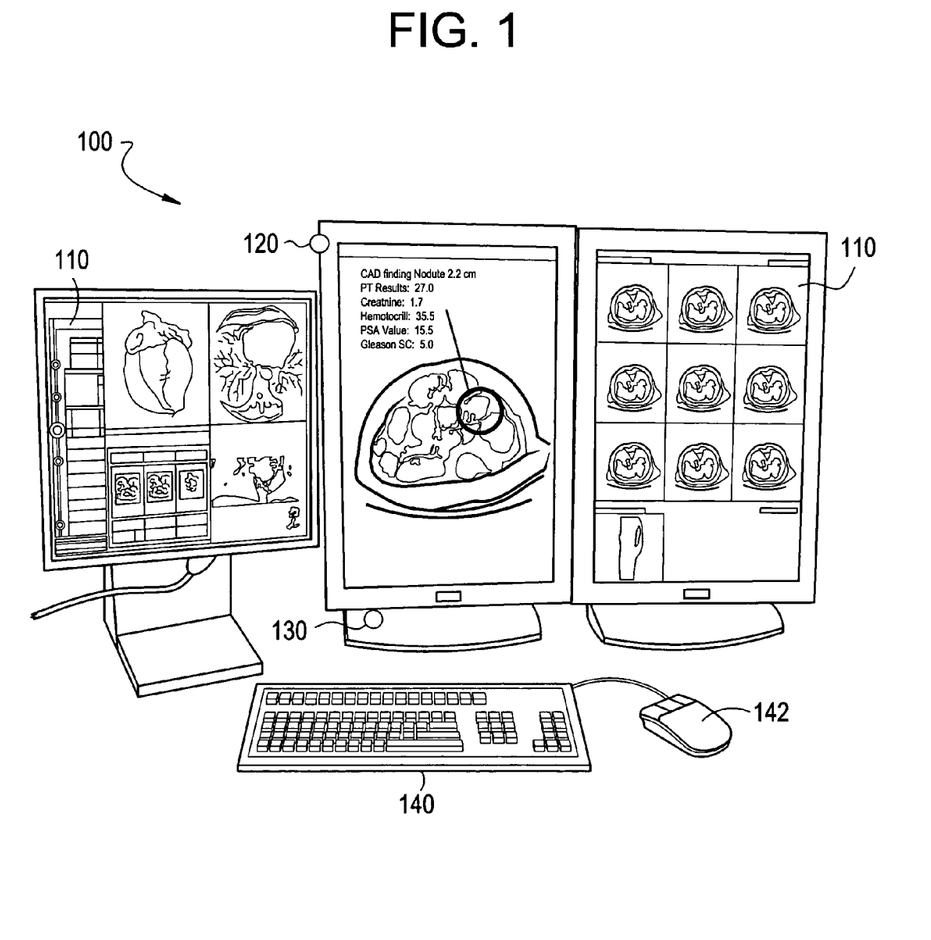
FIG. 1 illustrates an improved display system for selecting and displaying information in accordance with an embodiment of the present invention.

FIG. 1 illustrates an improved display system 100 for selecting and displaying information in accordance with an embodiment of the present invention. The system 100 includes a display 110, a motion tracking device 120, microphone 130, and manual input devices 140, 142. The components of the system 100 may communicate via wired, wireless and/or infrared communication, for example. The components of the system 100 may be implemented separately and/or integrated in various forms, for example.

As shown in FIG. 1, one or more simple display devices 110 may be used to display information to a user. The display 110 may be used with a portable eyewear and eye tracking system, such as a gaze tracking system including the motion tracking device 120, to display information for one or more users. By tracking where a user is focusing or fixating his or her visual attention, an accurate measure of user intent may be inferred. Eye or gaze tracking may be faster and more efficient than a mechanical pointing or selecting device, such as a keyboard 140 or mouse 142.

Additionally, voice commands and/or gesture control using cameras, such as fire-wire web cams, may allow interaction with imaging and information systems without disrupting a sterile field. The motion tracking device 120 may be used in conjunction with gesture control, for example. The microphone 130 may be used in conjunction with voice or subvocal command and control, for example.

The motion tracking device 120 may be a camera, for example. The motion tracking device 120 may work in conjunction with a headset or eyewear worn by a user, for example (not shown). The motion tracking device 120 may be attached to the display device 110, such as on a side or top of the display device 110.

A gaze tracking system may be based on a camera system (e.g., visible light or infrared), for example, and may be active or passive. Alternatively or in addition, a user's gaze may be tracked based on movement of the user's head via a camera or position sensor, for example. Multiple cameras may be used to track a location of a user's gaze. Additionally, multiple cameras may be used to drive a cursor or other indicator on a display, such as the display device 110. The gaze tracking system may include head gear, such as goggles or other ocular device, for a user to wear and/or may use a display-mounted camera or sensor, for example. In an embodiment, the gaze tracking system is calibrated for a user. By tracking a user's gaze, a system may initiate communication, selection, and/or function at a remote system, for example.

Figure 2:
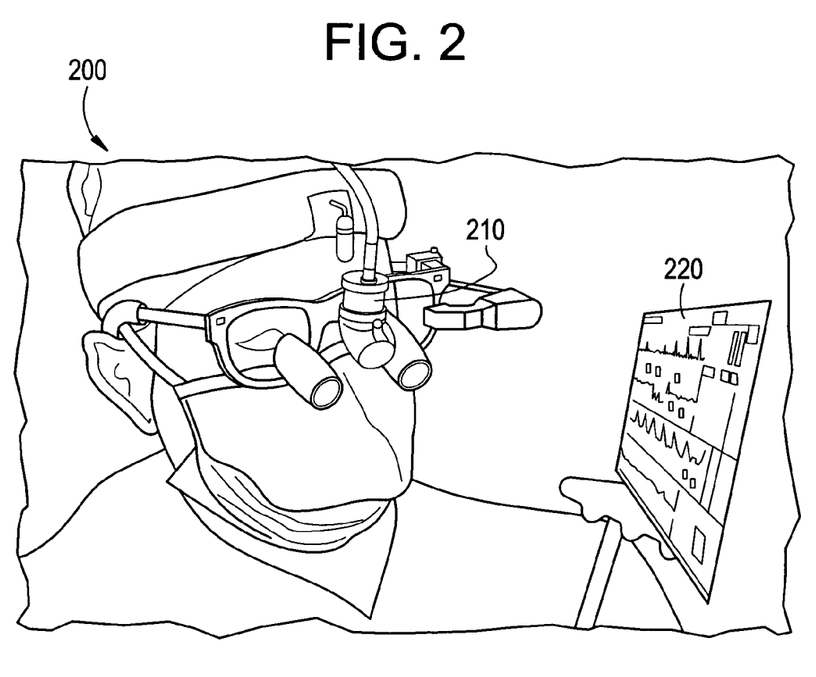
FIG. 2 depicts a portable eyewear viewing system used in accordance with an embodiment of the present invention.

FIG. 2 depicts a portable eyewear viewing system 200 used in accordance with an embodiment of the present invention. The system 200 includes an eyewear headset 210, a personal eyewear display 220, and a gaze tracking processor 230. The processor 230 may be integrated into the eyewear 210 and/or separate from the eyewear 210. The personal eyewear display 220 is projected in a user's field of view by the eyewear 210.

A healthcare practitioner may use eyewear 210, such as goggles, to capture the practitioner's gaze and perform interface navigation. A user's gaze may be tracked via infrared or other light source, for example. Light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

In an embodiment, goggles or other eyewear may also project images into a user's oculars or provide a miniature screen attached to the eyewear 210 and positioned in the user's field of vision to form a virtual personal display 220. Thus, eyewear 210 may be used to eliminate some displays in the healthcare environment. Additionally, eyewear 210 may allow specific information to be targeted for display for specific users in the healthcare environment. For example, a nurse, an anesthesiologist, and a surgeon receive different information displayed on their personal eyewear display 220. For example, a surgeon may view image-guided surgery and PACS data while an anesthesiologist views EKG and dosage data. In an embodiment, each user may view customized information without turning to look at a display to select the information.

In an embodiment, the eyewear 210 is a portable eyewear viewer that displays key dynamic patient information such as hemodynamic data, cardiology waveforms, vital signs, etc. Eyewear 210 allows a user to view information without turning his or her head to view an LCD or CRT monitor. Although the eyewear headset 210 allows users to view data while working "heads down" on a patient, resolution may be limited for image review and/or fine text review, for example. When a user wishes to view detailed information or a finer degree of granularity, the user may look at a larger display device in the healthcare environment.

An eye or gaze tracking capability of the headset 210 and/or processor 230 may be used to control a display device, such as the display device 110. For example, the processor 230 detects when a user is looking at a certain button, option or feature on a display and selects or activates the button, option or feature for the user. Activation of an option/feature may also be based on an amount of time a user is looking/has looked at a certain area. The eyewear system 200 may also be used in conjunction with voice commands and/or gestures to control the display device 110 and/or other systems or features, for example.

In an embodiment, a user looks at the display device 110. The gaze tracking processor 230 recognizes that the user wants to see certain information and displays context-sensitive information for the patient on the display device 110, for example. Information on gaze and/or head position may be relayed from the processor 230 to determine information on the display device 110. Additionally, user preference information, information from the display device 110, and/or other input may be transmitted to configure the contents and/or other parameters of the display device 110.

In an embodiment, information displayed on the display device 110 may be determined based on rules and/or perspectives, for example. For example, rules determine that a doctor's gaze takes precedence over a nurse's gaze. Then, when the doctor turns away from the display device 110, the nurse gains control of the display device 110. Alternatively, control of the display device 110 may be shared by multiple users and common information displayed on display device 110 so that multiple users may be accommodated at approximately the same time.

The processor 230 and/or other processor or system related to the display device 110 may have an ability to arbitrate conflicts and priority among a plurality of users seeking access determine which user(s) should take control of the display device 110. For example, rules-based display control and/or hanging protocols may govern which user has control and priority and/or which users may share control and display area. Rules and other protocols may also govern when control over the display device 110 is relinquished and/or preempted.

In an embodiment, video switchboxes and/or voice commands may be used with image-guided surgery to switch displays so that only image-guided surgery information is viewed. In an embodiment, voice control and/or gestures may be used in conjunction with eye tracking to control the display device 110 and/or a system cursor.

In an embodiment, a gaze tracking system and display device may work together with a rules-based context manager to filter and display information. One example of a rules-based context manager is described in a U.S. patent application filed on Oct. 1, 2004, entitled "System and Method for Rules-Based Context Management in Radiology and Cardiology Diagnostic Reading", with inventor Prakash Mahesh, which is herein incorporated by reference in its entirety.

In an embodiment, the gaze tracking system and display device may work together with a perspectives management system for handling multiple applications and workflow. The perspectives management system allows various perspectives to be defined which save workflow steps and other information for a particular user. Perspectives allow a personalized information display to present relevant information germane to a patient's current condition, for example. One example of a perspectives management system is described in a U.S. patent application filed on Oct. 1, 2004, entitled "System and Method for Handling Multiple Radiology Applications and Workflows", with inventors Prakash Mahesh and Mark Ricard, which is herein incorporated by reference in its entirety. For example, in a surgical OR there may be numerous healthcare practitioners at an OR table who use specific perspectives or views of relevant patient information. With a single, large format display (e.g., an LCD, plasma display, 46" display, etc.), each user has the ability to view their personal perspectives on the display in large and/or small format. The display may be shared among the users.

In an embodiment, the system 100 and/or system 200 may work in conjunction with one or more systems, such as diagnostic review workstations. Diagnostic review workstations may be used to access enterprise clinical information, for example. For example, a radiologist may access clinical information relevant to a current exam in a "just in time" fashion.

Using eye tracking input, hand gesture, voice commands, and/or other technologies, a user may communicate a request for clinical decision support for example. For example, by dwelling on a certain area of the display device 110 for a certain period of time, speaking a vocal or subvocal command such as "decision help", or other communication, a request for decision support may be conveyed to a processing system.

Once the processing system recognizes the command, relevant clinical information germane to a current "focus" or location (e.g., cursor location) on the display device 110 may be displayed on the display device 110. For example, if a radiologist identifies an unknown mass in a patient's kidney and focuses his or her gaze on the kidney, overlays may pop-up on the display device 110 to provide additional information and support to the radiologist. Information may include computer-aided detection (CAD) findings/region of interest (ROI), prothrombin time (PT) values, Creatinine levels, Gleason Score, family history, etc.

In an embodiment, gestures, gazing, voice command, and/or other activation related to a "reason for exam" trigger the processing system to retrieve relevant clinical information from disparate information systems, for example. Retrieved information may be cached or stored locally until used for presentation. Based on a general location of a cursor or other indicator on the display device 110, information relating to a kidney, lung, aorta, and/or other anatomy of interest may be displayed. The information may exist in a DICOM layer or may be saved in a DICOM layer if a user finds the information beneficial to a diagnosis and/or as evidence for a report.

Thus, activation of a command to display relevant enterprise information at the display device 110 which is germane to a specific location on the display device 110 displays enterprise information on the display device 110. In an embodiment, a user does not have to log-in and search disparate information systems but rather may access disparate systems from a single workstation using context sharing and/or other communication. Context specific information may appear on the display device 110, such as using a "roll-over" or caption effect. Information maybe filtered according to one or more rules and/or organized according to one or more perspectives, for example.

In an embodiment, the display device 110 is connected to or in communication with a workstation or computing system capable of aggregating information from disparate sources. Rather than access separate imaging and/or information systems to retrieve information, a user may retrieve information via the workstation through context sharing and networking, for example. When viewing one or more images via the display device 110, a user may be interested in additional information regarding the image(s) or part(s) of the image(s), for example.

Rather than manually positioning a cursor over an image or part of an image using a mousing device or keyboard, for example, a gaze tracking system may be used to indicate a location on the display device 110. That is, a gaze tracking system, such as one using the motion tracking device 120, may determine a focus of the user's gaze. The tracking system may also determine a "dwell time" or length of time that the user focuses on a location. If a user focuses on a location for at least a certain period of time, the tracking system may position a cursor at that location on the display device 110, for example. The tracking system may also activate a function with respect to the location and/or retrieve information based on the location, for example. In an embodiment, gazing at a certain location for a certain length of time generates a "roll-over" or overlay of supporting information at the display device 110. For example, if a radiologist is gazing at an image of a kidney, a roll-over is displayed to provide supporting information to allow the radiologist to better understand the case.

In an embodiment, gaze tracking may be combined with a rules-based system for information retrieval. Based on rules, such as system rules, user rules, procedure-based rules, and/or user preferences, relevant information may be retrieved and/or filtered. Information, such as laboratory results, patient history, reason for examination, referring physician comments, and/or other information, may be retrieved using a rules-based engine and displayed in conjunction with and/or overlaid on top of image(s) and/or information on the display device 110. Additionally, information may be added, deleted, modified and/or customized based user preferences, user habits, and/or external updates/input, for example. In an embodiment, by looking away from the display device 110, a user may trigger personal metric, communication functions, and/or other functionality apart from the display device 110, for example. In an embodiment, biometric (e.g., retina pattern, iris scan, voice authentication) or other authentication method may be used to verify access to information.

In an embodiment, a display area of the display device 110 is mapped with respect to a coordinate system, such as an x-y coordinate system. Areas in an image are mapped to x,y coordinates or other location information, for example. Mapping allows the system to determine what area of an image corresponds to the location of a user's gaze or cursor, for example. Then, the system may retrieve information related to the area in the image and/or on the display 110. The display device 110 and tracking system may be calibrated to map specific locations in specific types of exam studies, such as modality, body part, etc.

In an embodiment, gaze detection and tracking may be combined with click and/or voice/subvocal command, etc. to manipulate data on a display device and/or retrieve information. Gaze tracking, manual select, and/or vocal/subvocal command may be used to generate a structured report or other output from information displayed, for example. Data displayed via the display device 110 may be added to the report along with image(s), for example.

Figure 3:
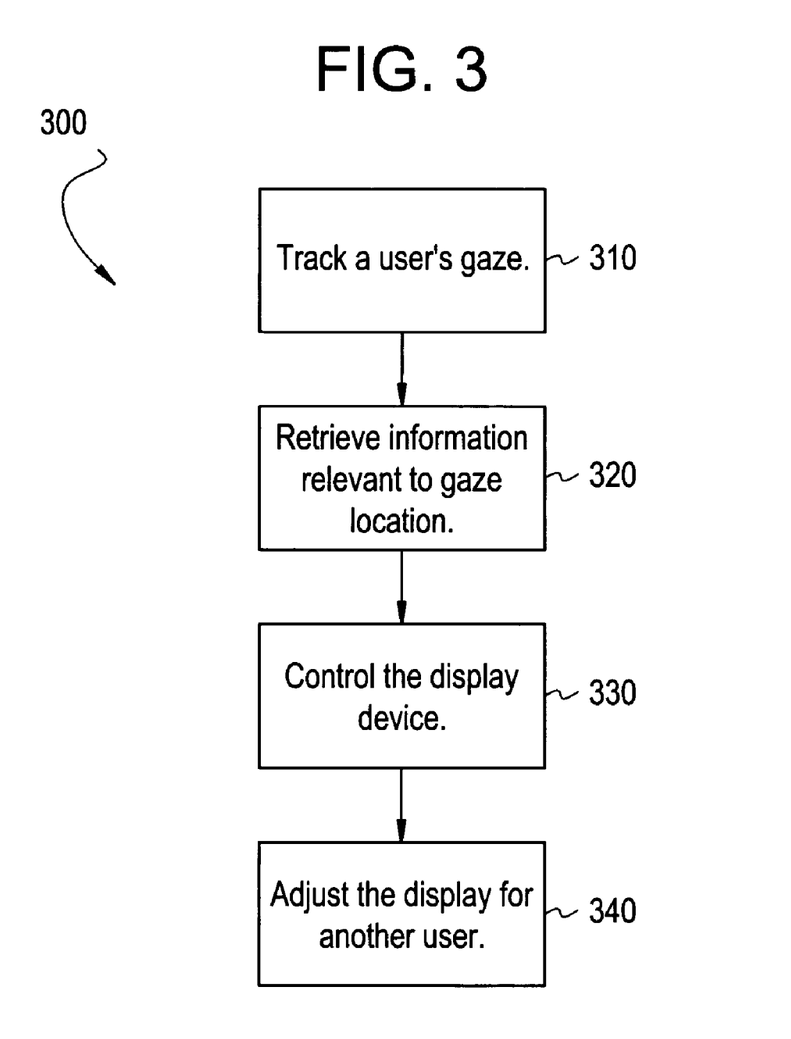
FIG. 3 shows a flow diagram for a method for gaze detection and control in a healthcare environment used in accordance with an embodiment of the present invention.

FIG. 3 shows a flow diagram for a method 300 for gaze detection and control in a healthcare environment used in accordance with an embodiment of the present invention. First, at step 310, a user's gaze is tracked. For example, the user's gaze may be tracked via eyewear and/or camera(s). The user's gaze may be tracked in relation to a display device to determine an area on the display device where the user is looking.

Then, at step 320, information relevant to the location at which the user is gazing is retrieved. For example, if the user is looking at an image of a chest scan, information related to the chest scan is retrieved. Information retrieval may be based on additional input from the user, such as manual input, vocal or subvocal input, and/or gestures, and/or settings, such as rules, preferences, filters, and/or perspectives. That is, context-sensitive perspectives and/or rules may be used to display relevant information for the particular user on the display device.

Next, at step 330, the display device may be further controlled by the user. For example, a user may activate functions, arrange displayed information, and/or retrieve additional information and/or applications on the display device and/or computing system(s) in communication with the display device. For example, the user may adjust information shown on the display device based on gaze, voice command, gesture, button, switch, and/or mousing device.

Space on the display device may be devoted entirely to a single user who is looking at the display device or may be divided to display data for multiple users. Alternatively, the display device may include an area displaying general data and one or more areas displaying data specific to a certain user. In an embodiment, if multiple users are looking toward the display device, user priority may be compared to determine which user(s) are allowed to take control of the display device.

At step 340, the display device may be adjusted by another user. For example, when the user redirects his or her gaze away from the display device, the display adjusts itself for another user. For example, when a surgeon looks from a large, overhead display back down to a patient undergoing a surgical procedure, the display becomes available for a nurse to display information.

Thus, certain embodiments unify a variety of information systems and other applications in a single display viewable by a plurality of users. Certain embodiments filter information available to a user based on rules and/or perspectives. Certain embodiments address information overload, ergonomic issues, and effects from multiple displays such as clutter, heat, expense, and luminosity from displays, for example. In certain embodiments, multiple displays may be eliminated from a healthcare environment, such as an OR, and information on a single display may be simplified to show relevant patient information to a particular practitioner.

Certain embodiments help provide clinical decision support to healthcare practitioners. Certain embodiments reduce time spent searching for clinical information. Additionally, certain embodiments provide value added, pre-emptive information for a healthcare practitioner, such as a radiologist or surgeon. Certain embodiments provide key clinical decision support that aids in diagnostic interpretation, for example. Thus, medical errors may be reduced and medical workflow may be streamlined, for example. Additionally, repetitive head and neck movements may be reduced by minimizing use of traditional manual input devices resulting in a reduction in ergonomic difficulties and stress disorders. Wireless and minimally invasive product design allows easy-to-use, comfortable interaction. Thus, certain embodiments allow users to naturally interact with image(s), interface(s) and/or other information on which they are focused.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A gaze detection and control system for displaying relevant enterprise, clinical or decision support information, said system comprising: an information system including information related to at least one image;
a display device capable of displaying images and data;
a gaze tracking system for detecting a location of a user's gaze with respect to said display device, wherein said gaze tracking system triggers a retrieval of information from said information system based at least in part on said location of said user's gaze, wherein said retrieved information is displayed at said display device;
a plurality of perspectives, each perspective saving a relation with at least one of a plurality of information sources;
a medical perspectives manager for associating at least one information source with a perspective, wherein the medical perspectives manager allows a user to access the at least one associated information source using the perspective;
a rules engine including at least one rule governing at least one of availability and presentation of information based at least in part on the user's gaze; and
a context manager for obtaining information from the plurality of information sources based on a query and filtering the information based on the at least one rule.

2. The system of claim 1, wherein said retrieved information is overlaid over an image at said display device.

3. The system of claim 1, wherein said gaze tracking system comprises at least one of a camera and eyewear.

4. The system of claim 1, farther including a conflict resolution module for determining priority and control of the display device among a plurality of users.

5. The system of claim 1, wherein a function at the display is triggered using at least one of a voice command, a gesture, and a gaze.

6. A method for displaying medical information based on gaze detection, said method comprising:
determining a location of a user's gaze in relation to a reference position;
defining at least one perspective personalizing information relevant to said user;
updating information on a display device based on said user's gaze; and
filtering information available at said display device based on at least one rule, said rule based at least in part on said user's gaze;
wherein information is updated on said display device based on at least one of preferences and input from said user.

7. The method of claim 6, further comprising arbitrating between a plurality of users to determine control of said display device.

8. The method of claim 6, further comprising allowing multiple users to control information at said display device.

9. The method of claim 6, further comprising triggering a function at said display device using at least one of a voice command, a gesture, and a gaze.

10. The method of claim 6, further comprising overlaying information on information previously displayed at said display device.

11. A computer-readable storage medium including a set of instructions for execution on a computer, the set of instructions comprising:
a gaze detection routine for determining a gaze location at which a user is looking at a display; and
a display routine for displaying, on the display, information associated with the gaze location;
a rules-based context management routine for selecting and filtering said information for display based at least in part on the gaze location; and
a perspectives management routine for customizing layout of the information for display;
wherein said instructions, when executed on a computer, facilitate the display of information on a display device based on the user gaze location.

12. The set of instructions of claim 11, wherein said information includes at least one of data and an image.

13. The set of instructions of claim 11, wherein said gaze detection routine maps the gaze location at the display to a location in content displayed by the display routine.

* * * * *

UNITED STATES PATENT AND TRADEMARK OFFICE
CERTIFICATE OF CORRECTION

PATENT NO. : 7,501,995 B2  Page 1 of 1
APPLICATION NO. : 11/039152
DATED : March 10, 2009
INVENTOR(S) : Mark M. Morita, Prakash Mahesh and Thomas A. Gentles

Figure 4:
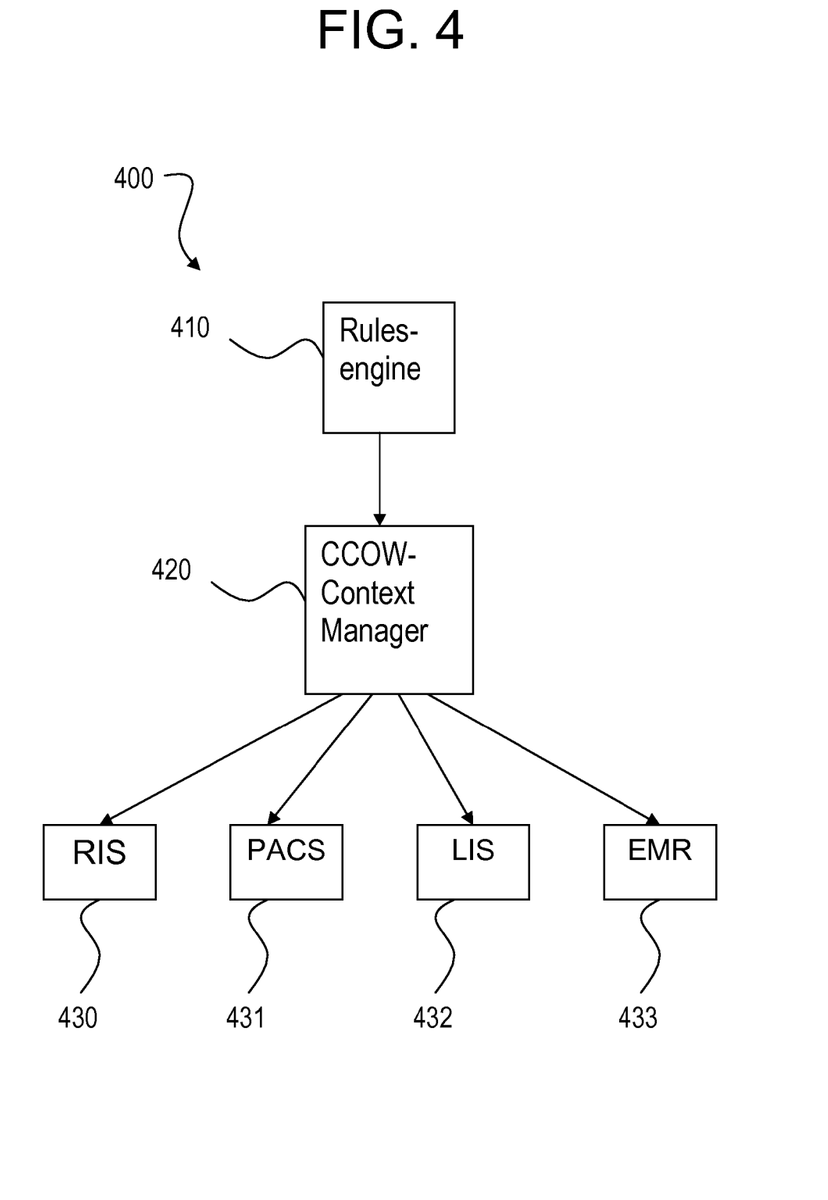
FIG. 4 illustrates a rules-based context management system 400 used in accordance with an embodiment of the present technology. The system 400 includes a rules engine 410, a context manager 420, and a plurality of information systems 430, 431, 432, 433. Information systems 430-433 may include a radiology information system (RIS) 430, a picture archiving and communication system (PACS) 431, a laboratory information system (LIS) 432, and/or an electronic medical record (EMR) 433, for example. The context manager 420 may be a clinical context object workgroup (CCOW) context manager, for example. The components of the system 100 may communicate via wired and/or wireless connections on one or more processing units, such as computers, medical systems, storage devices, custom processors, and/or other processing units. In an embodiment, the components of the system 400 are integrated into a single unit.

It is certified that error appears in the above-identified patent and that said Letters Patent is hereby corrected as shown below:

At col. 5, lines 59 to col. 6, line 8, please delete the complete paragraph and insert -- FIG. 4 shows a rules-based context management system used in accordance with an embodiment of the present technology. --

At col. 8, end of line 34, new paragraph, insert -- FIG. 4 illustrates a rules-based context management system 400 used in accordance with an embodiment of the present technology. The system 400 includes a rules engine 410, a context manager 420, and a plurality of information systems 430, 431, 432, 433. Information systems 430-433 may include a radiology information system (RIS) 430, a picture archiving and communication system (PACS) 431, a laboratory information system (LIS) 432, and/or an electronic medical record (EMR) 433, for example. The context manager 420 may be a clinical context object workgroup (CCOW) context manager, for example. The components of the system 100 may communicate via wired and/or wireless connections on one or more processing units, such as computers, medical systems, storage devices, custom processors, and/or other processing units. In an embodiment, the components of the system 400 are integrated into a single unit. --

Signed and Sealed this

Twelfth Day of May, 2009

JOHN DOLL
*Acting Director of the United States Patent and Trademark Office*